(12) United States Patent
Pelzer

(10) Patent No.: US 10,669,508 B2
(45) Date of Patent: Jun. 2, 2020

(54) USE OF 1-[(4R)-4-METHYLCYCLOHEXEN-1-YL]ETHANONE AS AN AROMA CHEMICAL

(71) Applicant: BASF SE, Ludwigshafen am Rhein (DE)

(72) Inventor: Ralf Pelzer, Lampertheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 16/344,646

(22) PCT Filed: Oct. 25, 2017

(86) PCT No.: PCT/EP2017/077305
§ 371 (c)(1),
(2) Date: Apr. 24, 2019

(87) PCT Pub. No.: WO2018/077947
PCT Pub. Date: May 3, 2018

(65) Prior Publication Data
US 2019/0300820 A1  Oct. 3, 2019

(30) Foreign Application Priority Data
Oct. 28, 2016  (EP) .................................. 16196213

(51) Int. Cl.
| | | |
|---|---|---|
| *A61Q 13/00* | (2006.01) | |
| *A61K 8/18* | (2006.01) | |
| *A61K 8/00* | (2006.01) | |
| *C11B 9/00* | (2006.01) | |
| *C07C 49/337* | (2006.01) | |
| *C07C 49/543* | (2006.01) | |
| *A61K 8/35* | (2006.01) | |

(52) U.S. Cl.
CPC .............. *C11B 9/0034* (2013.01); *A61K 8/35* (2013.01); *A61Q 13/00* (2013.01); *C07C 49/337* (2013.01); *C07C 49/543* (2013.01)

(58) Field of Classification Search
CPC ......... C11B 9/0034; A61Q 13/00; A61K 8/35; C07C 49/337; C07C 49/543
USPC .............................................. 512/24, 22, 8, 1
See application file for complete search history.

(56) References Cited

U.S. PATENT DOCUMENTS

2014/0023770 A1* 1/2014 Holscher ................ A61Q 13/00
426/538

FOREIGN PATENT DOCUMENTS

WO    WO-2017044957 A1    3/2017

OTHER PUBLICATIONS

Dolby, et al., "Studies of Terpene Chemistry. I. The Acid-Catalyzed Dimerization of Citronellal", Journal of Organic Chemistry, vol. 29, Issue 8, 1964, pp. 2306-2310.
European Search Report for EP Patent Application No. 16196213.9, dated Jan. 2, 2017, 2 pages.
Rupe, et al., "4-Methyl-1-äthinyl-cyclohexanol und seine Umwandlung zum 4-Methyl-cyclohexen-methyl-keton", Helevetica Chimica Acta, vol. 14, Issue 4, Jul. 1, 1931, pp. 701-708.
Taber, et al., "Branching strategy in organic synthesis. A versatile ketone to enone homologation", The Journal of Organic Chemistry, vol. 44, Issue 3, 1979, pp. 450-452.
International Search Report for PCT/EP2017/077305 dated Nov. 24, 2017.
Written Opinion of the International Searching Authority for PCT/EP2017/077305 dated Nov. 24, 2017.

* cited by examiner

*Primary Examiner* — Jessica Whiteley
(74) *Attorney, Agent, or Firm* — Faegre Drinker Biddle & Reath LLP

(57) ABSTRACT

Use of 1-[(4R)-4-methylcyclohexen-1-yl]ethanone to impart a ylang-ylang note to a composition.

9 Claims, No Drawings

USE OF 1-[(4R)-4-METHYLCYCLOHEXEN-1-YL]ETHANONE AS AN AROMA CHEMICAL

CROSS-REFERENCE TO RELATED APPLICATIONS

This application is a national stage application (under 35 U.S.C. § 371) of PCT/EP2017/077305, filed Oct. 25, 2017, which claims benefit of European Application No. 16196213.9, filed Oct. 28, 2016, both of which are incorporated herein by reference in their entirety.

The present invention relates to the use of 1-[(4R)-4-methylcyclohexen-1-yl]ethanone or a mixture which comprises 1-[(4R)-4-methylcyclohexen-1-yl]ethanone as an aroma chemical, in particular to impart a ylang-ylang note. The present invention also relates to compositions, preferably perfume compositions, body care compositions, hygiene articles, household cleaning compositions, textile detergent compositions, foods and food supplements comprising 1-[(4R)-4-methylcyclohexen-1-yl]ethanone.

BACKGROUND OF THE INVENTION

Aroma chemicals, especially fragrances are of great interest especially in the field of cosmetics and cleaning and laundry compositions. Fragrances of natural origin are mostly expensive, often limited in their available amount and, on account of fluctuations in environmental conditions, are also subject to variations in their content, purity etc. To circumvent these undesirable factors, it is therefore of great interest, by way of example, to chemically modify readily available natural substances, e.g. readily available fragrances of natural origin, to create substances, which have organoleptic properties that resembles more expensive natural fragrances or which have novel and interesting organoleptic profiles. Such "semi-synthetic" substances can, by way of example, be used as substitutes for purely natural substances on account of their odor, where substitute and natural substance do not necessarily have to have a chemical-structural similarity.

However, since even small changes in chemical structure may bring about massive changes in the sensory properties such as odor and also taste, the targeted search for substances with certain sensory properties such as a certain odor is extremely difficult. The search for new fragrances and flavors is therefore in most cases difficult and laborious without knowing whether a substance with the desired odor and/or taste will even actually be found. There is a constant need for novel aroma chemicals with advantageous sensory properties.

Ylang-ylang oil has a long history of fragrance and food flavoring use. Ylang-ylang oil is obtained by steam distillation of the flowers of the Ylang-Ylang tree, *Cananga odorata*. The oil from ylang-ylang is widely used in perfumery for oriental themed perfumes (such as Chanel No. 5). The main aromatic components of ylang-ylang oil are benzyl acetate, linalool, p-cresyl methyl ether, and methyl benzoate, responsible for its characteristic odor. Ylang-ylang oil or p-methyl-cresylether have been used to impart the characteristic, desirable note (the so called "ylang ylang note") to many compositions, such as e.g. perfume compositions, body care compositions, hygiene articles, household cleaning compositions, textile detergent compositions, foods and food supplements. Due to the limited availability of the natural source of the ylang-ylang oil, but especially due to the toxicological concerns of p-methyl-cresylether, there is a constant need for an aroma chemical, which can impart a ylang-ylang note to a composition and which at the same time is suitable for compositions that are in direct contact with the human skin.

Rupe et al. (Helevetica Chimica Acta, 1931, 14, 701-708) disclose on page 702, formula III 1-[4-methylcyclohexen-1-yl]ethanone without any information regarding the stereochemistry. From the described method of synthesis of the substance of formula III it is chemically compulsory, that the substance of formula III can only be a racemic mixture. Rupe et al. on page 704 attribute a "fine, strong, roselike odor" to this racemic mixture. Rupe et al. does not provide any hint or information that 1-[(4R)-4-methylcyclohexen-1-yl]ethanone can be used to impart a ylang-ylang note to a composition.

Dolby et al. (J. Org. Chem, 29, 2306, 1964) on bridging columns of page 2306 to page 2307 describe the preparation of 1-acetyl-4-methylcyclohexene by ozonolysis of the dimer which is formed during acid catalyzed dimerization of (+)-Citronellal. 1-[(4R)-4-methylcyclohexen-1-yl]ethanone itself is disclosed in Taber et al. (J. Org. Chem., 44, No 3, 450-452, 1979) page 450, formula 11. Neither reference discloses the use of 1-[(4R)-4-methylcyclohexen-1-yl]ethanone according to the invention.

SUMMARY OF THE INVENTION

It was an object of the present invention to provide a substance, which can be used to impart a ylang-ylang note to a composition. The aroma chemical should be free from toxicological concerns. It was a further object of the present invention to provide a substance, which can be used as an aroma chemical in compositions, perfume compositions, body care compositions, hygiene articles, household cleaning compositions, textile detergent compositions, foods, food supplements, pharmaceutical compositions or crop protection compositions. In particular, odor-intensive substances having a pleasant odor are sought.

It was surprisingly found that, 1-[(4R)-4-methylcyclohexen-1-yl]ethanone exhibits pleasant organo-leptical properties and can advantageously be used as a fragrance or as flavor. It was surprisingly found, that 1-[(4R)-4-methylcyclohexen-1-yl]ethanone is suitable for imparting a ylang-ylang note to a composition.

The present invention relates to the use of 1-[(4R)-4-methylcyclohexen-1-yl]ethanone to impart a ylang-ylang note to a composition.

The present invention further relates to the use of 1-[(4R)-4-methylcyclohexen-1-yl]ethanone as substitute for p-Methyl-cresyl-ether.

The present invention further relates to the use of 1-[(4R)-4-methylcyclohexen-1-yl]ethanone as an aroma chemical in a composition selected from perfume compositions, body care compositions, hygiene articles, household cleaning compositions, textile detergent compositions, foods, food supplements, pharmaceutical composition and crop protection composition.

The present invention further relates to a mixture comprising 1-[(4R)-4-methylcyclohexen-1-yl]ethanone and 1-[(4S)-4-methylcyclo-hexen-1-yl]ethanone, wherein the amount of 1-[(4R)-4-methylcyclohexen-1-yl]ethanone exceeds the amount of 1-[(4S)-4-methylcyclohexen-1-yl]ethanone.

The present invention further relates to a composition comprising 1-[(4R)-4-methylcyclohexen-1-yl]ethanone and at least one further aroma chemical.

The present invention further relates to a composition comprising 1-[(4R)-4-methylcyclohexen-1-yl]ethanone and at least one compound selected from the group consisting of surfactants, oil components and solvents.

The present invention further relates to a method of preparing a perfume composition, body care composition, hygiene article, household cleaning composition, textile detergent composition, food, food supplement, pharmaceutical composition or crop protection composition, comprising including 1-[(4R)-4-methylcyclohexen-1-yl]ethanone in a perfume composition, body care composition, hygiene article, household cleaning composition, textile detergent composition, food, food supplement, pharmaceutical composition or crop protection composition.

1-[(4R)-4-methylcyclohexen-1-yl]ethanone and the mixtures of its stereoisomers predominantly containing the 4R isomer exhibit the following advantages:

they possess advantageous sensory properties, in particular a pleasant odor, more specifically they possess an odor of the ylang-ylang type. Therefore, they can be favorably used as an aroma chemical in perfume compositions, body care compositions, hygiene articles, household cleaning compositions, textile detergent compositions, foods, food supplements, pharmaceutical composition or crop protection composition or to impart a ylang-ylang note to a composition.

by virtue of its physical properties, 1-[(4R)-4-methylcyclohexen-1-yl]ethanone and the mixtures of its stereoisomers predominantly containing the 4R isomer has particularly good, virtually universal solvent properties for other fragrances and other customary ingredients in fragrance-comprising preparations such as, in particular, perfumes.

1-[(4R)-4-methylcyclohexen-1-yl]ethanone and the mixtures of its stereoisomers predominantly containing the 4R isomer can be produced by using the readily obtainable starting materials material L-Isopulegol [=(1R,2S,5R)-2-Isopropenyl-5-methylcyclohexanol] or mixtures of D/L-Isopulegol [2-Isopropenyl-5-methylcyclohexanol]

11-[(4R)-4-methylcyclohexen-1-yl]ethanone and the mixtures of its stereoisomers predominantly containing the 4R isomer is likely to have low toxicity as it belongs to a group of oxidation products of which are in general free from toxicological concerns.

DETAILED DESCRIPTION OF THE INVENTION

One embodiment of the invention relates to the use of 1-[(4R)-4-methylcyclohexen-1-yl]ethanone to impart a ylang-ylang note to a composition. One embodiment of the invention relates to the use of 1-[(4R)-4-methylcyclohexen-1-yl]ethanone as a substitute for p-Methyl-cresyl-ether (=4-Methoxytoluol).

1-[(4R)-4-methylcyclohexen-1-yl]ethanone is a substance of the following formula (I)

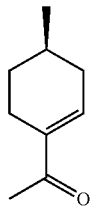

(I)

A further embodiment of the invention relates to a mixture comprising 1-[(4R)-4-methylcyclohexen-1-yl]ethanone and 1-[(4S)-4-methylcyclo-hexen-1-yl]ethanone, wherein the amount of 1-[(4R)-4-methylcyclohexen-1-yl]ethanone exceeds the amount of 1-[(4S)-4-methylcyclohexen-1-yl]ethanone.

The term "4R-isomer" in the context of the present invention denotes the substance 1-[(4R)-4-methylcyclohexen-1-yl]ethanone. The term "4S-isomer" the context of the present invention denotes the substance 1-[(4S)-4-methylcyclohexen-1-yl]ethanone.

More specifically, in these mixtures, the 4R-isomer is present in an amount of at least 55% by weight, in particular of at least 65% by weight, based on the total weight of the 4R- and 4S-isomers.

More specifically, in these mixtures, the 4R-isomer is present in an amount of at least 70% by weight, in particular of at least 75% by weight, more particular in an amount of at least 80% by weight, based on the total weight of the 4R- and 4S-isomers.

In a preferred embodiment of the invention in these mixtures, the 4R-isomer is present in an amount of at least 90% by weight, in particular of at least 95% by weight, more particular of at least 97% by weight, more particular of at least 99% by weight, based on the total weight of the 4R- and 4S-isomers.

Due to its sensory properties, 1-[(4R)-4-methylcyclohexen-1-yl]ethanone can be advantageously used in composition selected from perfume compositions, body care compositions, hygiene articles, household cleaning compositions, textile detergent compositions, foods, food supplements, pharmaceutical compositions or crop protection compositions.

A further embodiment of the invention therefore relates to the use of 1-[(4R)-4-methylcyclohexen-1-yl]ethanone as an aroma chemical.

A further embodiment of the invention therefore relates to the use of 1-[(4R)-4-methylcyclohexen-1-yl]ethanone as an aroma chemical in a composition selected from perfume compositions, body care compositions, hygiene articles, household cleaning compositions, textile detergent compositions, foods, food supplements, pharmaceutical compositions or crop protection compositions.

The term "aroma chemical" denotes a substance which is used to obtain a sensory impression, and encompasses its use in fragrance and/or flavor compositions. A fragrance composition being a composition, which predominately induces an odor impression, a flavor composition being a composition, which predominantly induces a taste impression.

Due to its physical properties, 1-[(4R)-4-methylcyclohexen-1-yl]ethanone and the mixtures of stereoisomers predominantly containing the 4R-isomer have particularly good, virtually universal solvent properties for other aroma chemicals.

A further embodiment of the invention therefore relates to a composition comprising 1-[(4R)-4-methylcyclohexen-1-yl]ethanone and at least one further aroma chemical.

The further aroma chemical can for example be one, preferably 2, 3, 4, 5, 6, 7, 8 or further aroma chemicals, selected from the group consisting of:

Geranyl acetate (3,7-Dimethyl-2,6 octadien-1yl acetate), alpha-hexylcinnamaldehyde, 2-phenoxyethyl isobutyrate (Phenirat[1]), dihydromyrcenol (2,6-dimethyl-7-octen-2-ol), methyl dihydrojasmonate (preferably with a content of cis isomer of more than 60% by weight) (Hedione[9], Hedione HC[9]), 4,6,6,7,8,8-hexamethyl-1,3,4,6,7,8-hexahydrocyclopenta[g]benzopyran (Galaxolid[3]), tetrahydrolinalool (3,7- dimethyloctan-3-ol), ethyllinalool, benzyl salicylate, 2-methyl-3-(4-tert-butylphenyl)propanal (Lilial[2]), cinnamyl alcohol, 4,7-methano-3a,4,5,6,7,7a-hexahydro-5-indenyl acetate and/or 4,7-methano-3a,4,5,6,7,7a-hexahydro-6-indenyl acetate (Herbaflorat[1]), citronellol, citronellyl acetate, tetrahydrogeraniol, vanillin, linalyl acetate, styrolyl acetate (1-phenylethyl acetate), octahydro-2,3,8,8-tetramethyl-2-acetonaphthone and/or 2-acetyl-1,2,3,4,6,7,8-octahydro-2,3,8,8-tetramethylnaphthalene (Iso E Super[3]), hexyl salicylate, 4-tert-butylcyclohexyl acetate (Oryclone[1]), 2-tert-butylcyclohexyl acetate (Agrumex HC[1]), alpha-ionone (4-(2,2,6-trimethyl-2-cyclohexen-1-yl)-3-buten-2-one), n-alpha-methylionone, alpha-isomethylionone, coumarin, terpinyl acetate, 2-phenylethyl alcohol, 4-(4-hydroxy-4-methylpentyl)-3-cyclohexenecarboxaldehyde (Lyral[3]), alpha-amylcinnamaldehyde, ethylene brassylate, (E)- and/or (Z)-3-methylcyclopentadec-5-enone (Muscenon[9]), 15-pentadec-11-enolide and/or 15-pentadec-12-enolide (Globalide[1]), 15-cyclopentadecanolide (Macrolide[1]), 1-(5,6,7,8-tetrahydro-3,5,5,6,8,8-hexamethyl-2-naphthalenyl)ethanone (Tonalid[10]), 2-isobutyl-4-methyltetrahydro-2H-pyran-4-ol (Florol[9]), 2-ethyl-4-(2,2,3-trimethyl-3-cyclopenten-1-yl)-2-buten-1-ol (Sandolen[1]), cis-3-hexenyl acetate, trans-3-hexenyl acetate, trans-2/cis-6-nonadienol, 2,4-dimethyl-3-cyclohexenecarboxaldehyde (Vertocitral[1]), 2,4,4,7-tetramethyloct-6-en-3-one (Clark tone[1]), 2,6-dimethyl-5-hepten-1-al (Melonal[2]), borneol, 3-(3-isopropylphenyl) butanal (Florhydral[2]), 2-methyl-3-(3,4-methylenedioxyphenyl)propanal (Helional[3]), 3-(4-ethylphenyl)-2,2-dimethylpropanal (Florazon[1]), 7-methyl-2H-1,5-benzodioxepin-3(4H)-one (Calone[1951 5]), 3,3,5-trimethylcyclohexyl acetate (preferably with a content of cis isomers of 70% by weight) or more and 2,5,5-trimethyl-1,2,3,4,4a,5,6,7-octahydronaphthalen-2-ol (Ambrinol S[1]). Within the context of the present invention, the aforementioned aroma chemical(s) are accordingly preferably combined with 1-[(4R)-4-methylcyclohexen-1-yl]ethanone according to the invention.

[1] trade name of Sym rise GmbH, Germany;
[2] trade name of Givaudan AG, Switzerland;
[3] trade name of International Flavors & Fragrances Inc., USA;
[5] trade name of Danisco Seillans S.A., France;
[9] trade name of Firmenich S.A., Switzerland;
[10] trade name of PFW Aroma Chemicals B.V., the Netherlands.

A further embodiment of the invention relates to a composition comprising 1-[(4R)-4-methylcyclohexen-1-yl]ethanone and at least one further aroma chemical selected from the group consisting of methyl benzoate, benzyl acetate, geranyl acetate, 2-isobutyl-4-methyltetrahydro-2H-pyran-4-ol and linalool.

A further embodiment of the invention relates to a composition comprising 1-[(4R)-4-methylcyclohexen-1-yl]ethanone and 2-isobutyl-4-methyltetrahydro-2H-pyran-4-ol.

A further embodiment of the invention relates to a composition comprising 1-[(4R)-4-methylcyclohexen-1-yl]ethanone and methyl benzoate.

Where trade names are given above, these refer to the following sources:

Further aroma chemicals with which 1-[(4R)-4-methylcyclohexen-1-yl]ethanone can be combined e.g. to give a composition according to the invention can be found e.g. in S. Arctander, Perfume and Flavor Chemicals, Vol. I and II, Montclair, N.J., 1969, self-published or K. Bauer, D. Garbe and H. Surburg, Common Fragrance and Flavor Materials, 4th Ed., Wiley-VCH, Weinheim 2001. Specifically, mention may be made of:

extracts from natural raw materials such as essential oils, concretes, absolutes, resins, resinoids, balsams, tinctures such as e.g.

ambergris tincture; amyris oil; *angelica* seed oil; *angelica* root oil; aniseed oil; valerian oil; basil oil; tree moss absolute; bay oil; mugwort oil; benzoin resin; bergamot oil; beeswax absolute; birch tar oil; bitter almond oil; savory oil; buchu leaf oil; cabreuva oil; cade oil; calmus oil; camphor oil; *cananga* oil; cardamom oil; cascarilla oil; *cassia* oil; *cassia* absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; Eau de brouts absolute; oak moss absolute; elemi oil; tarragon oil; *eucalyptus citriodora* oil; *eucalyptus* oil; fennel oil; pine needle oil; *galbanum* oil; *galbanum* resin; geranium oil; grapefruit oil; guaiacwood oil; gurjun balsam; gurjun balsam oil; helichrysum absolute; helichrysum oil; ginger oil; iris root absolute; iris root oil; jasmine absolute; calmus oil; camomile oil blue; roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linalool oil; *litsea cubeba* oil; laurel leaf oil; mace oil; marjoram oil; mandarin oil; *massoia* bark oil; *mimosa* absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange blossom absolute; orange oil; *origanum* oil; palmarosa oil; patchouli oil; *perilla* oil; peru balsam oil; parsley leaf oil; parsley seed oil; petitgrain oil; peppermint oil; pepper oil; pimento oil; pine oil; pennyroyal oil; rose absolute; rose wood oil; rose oil; rosemary oil; Dalmatian sage oil; Spanish sage oil; sandalwood oil; celery seed oil; spike-lavender oil; star anise oil; *styrax* oil; *tagetes* oil; fir needle oil; tea tree oil; turpentine oil; thyme oil; tolubalsam; tonka absolute; tuberose absolute; vanilla extract; violet leaf absolute; *verbena* oil; vetiver oil; juniper berry oil; wine lees oil; wormwood oil; winter green oil; hyssop oil; civet absolute; cinnamon leaf oil; cinnamon bark oil, and fractions thereof, or ingredients isolated therefrom; individual fragrances from the group of hydrocarbons, such as e.g. 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

the aliphatic alcohols such as e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

the aliphatic aldehydes and acetals thereof such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; (E/Z)-1-(1-methoxypropoxy)-hex-3-ene; the aliphatic ketones and oximes thereof such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

the aliphatic sulfur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitriles such as e.g. 2-nonenenitrile; 2-undecenenitrile; 2-tridecenenitrile; 3,12-tridecadienenitrile; 3,7-dimethyl-2,6-octadienenitrile; 3,7-dimethyl-6-octenenitrile;

the esters of aliphatic carboxylic acids such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxy acetate; methyl-3,7-dimethyl-2,6-octadienoate; 4-methyl-2-pentyl crotonate;

the acyclic terpene alcohols such as e.g. geraniol; nerol; linalool; lavandulol; nerolidol; farnesol; tetrahydrolinalool; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

the acyclic terpene aldehydes and ketones such as e.g. geranial; neral; citronellal; 7-hydroxy-3,7-dimethyloctanal; 7-methoxy-3,7-dimethyloctanal; 2,6,10-trimethyl-9-undecenal; geranyl acetone; as well as the dimethyl- and diethyl-acetals of geranial, neral, 7-hydroxy-3,7-dimethyloctanal;

the cyclic terpene alcohols such as e.g. menthol; isopulegol; alpha-terpineol; terpine-4-ol; menthan-8-ol; menthan-1-ol; menthan-7-ol; borneol; isoborneol; linalool oxide; nopol; cedrol; ambrinol; vetiverol; guajol; and the formates, acetates, propionates, isobutyrates, butyrates, isovalerates, pentanoates, hexanoates, crotonates, tiglinates and 3-methyl-2-butenoates thereof;

the cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalene-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedar wood oil (methyl cedryl ketone);

the cyclic alcohols such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols such as e.g. alpha-3,3-trimethyl-cyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers such as e.g. cineol; cedryl methyl ether; cyclododecyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9-trimethyldodecahydronaphtho[2,1-b]furan; 1,5,9-trimethyl-13-oxabicyclo-[10.1.0]trideca-4,8-diene; rose oxide; 2-(2,4-dimethyl-3-cyclohexen-1-yl)-5-methyl-5-(1-methylpropyl)-1,3-dioxane;

the cyclic and macrocyclic ketones such as e.g. 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclohexadecen-1-one; 7-cyclohexadecen-1-one; (7/8)-cyclohexadecen-1-one; 9-cycloheptadecen-1-one; cyclopentadecanone; cyclohexadecanone;

the cycloaliphatic aldehydes such as e.g. 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexene carbaldehyde; 4-(4-methyl-3-penten-1-yl)-3-cyclohexenecarbaldehyde;

the cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl (2,4-dimethyl-3-cyclohexen-1-yl) ketone;

the esters of cyclic alcohols such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

the esters of cycloaliphatic alcohols such as e.g. 1-cyclohexylethyl crotonate;

the esters of cycloaliphatic carboxylic acids such as e.g. allyl 3-cyclohexylpropionate; allyl cyclohexyloxyacetate; cis- and trans-methyl dihydrojasmonate; cis- and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

the araliphatic alcohols such as e.g. benzyl alcohol; 1-phenylethyl alcohol, 2-phenylethyl alcohol, 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl- 5-phenylpentanol; 3-methyl-5-phenyl pentanol; 3-phenyl-2-propen-1-ol; 4-methoxybenzyl alcohol; 1-(4-isopropylphenyl)ethanol;

the esters of araliphatic alcohols and aliphatic carboxylic acids such as e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

the araliphatic ethers such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]-m-dioxine;

the aromatic and araliphatic aldehydes such as e.g. benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 2-methyl-3-(4-isobutylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones such as e.g. acetophenone; 4-methylacetophenone; 4-methoxyacetophenone; 4-tert-butyl-2,6-di methylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tertbutyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

the aromatic and araliphatic carboxylic acids and esters thereof such as e.g. benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-di hydroxy-3,6-dimethylbenzoate; ethyl 3-phenylglycidate; ethyl 3-methyl-3-phenylglycidate;

the nitrogen-containing aromatic compounds such as e.g. 2,4,6-trinitro-1,3-dimethyl-5-tertbutylbenzene; 3,5-dinitro-2,6-dimethyl-4-tert-butylacetophenone; cinnamonitrile; 3-methyl-5-phenyl-2-pentenonitrile; 3-methyl-5-phenylpentanonitrile; methyl anthranilate; methyl-N-methylanthranilate; Schiff bases of methyl anthranilate with 7-hydroxy-3,7-dimethyloctanal, 2-methyl-3-(4-tert-butylphenyl) propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; skatole; 2-methoxy-3-isopropylpyrazine; 2-isobutyl-3-methoxypyrazine;

the phenols, phenyl ethers and phenyl esters such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

the heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

A further embodiment of the invention is directed to a composition comprising 1-[(4R)-4-methylcyclohexen-1-yl] ethanone and at least one compound selected from the group consisting of surfactants, emollients and solvents.

A further embodiment of the invention is directed to a composition comprising 1-[(4R)-4-methylcyclohexen-1-yl] ethanone and at least one compound selected from the group consisting of surfactants, emollients and solvents, wherein the solvent is not diethylether.

One embodiment of the invention is directed to a composition comprising 1-[(4R)-4-methylcyclohexen-1-yl]ethanone and at least one solvent.

One embodiment of the invention is directed to a composition comprising 1-[(4R)-4-methylcyclohexen-1-yl]ethanone and at least one solvent, wherein the solvent is not diethylether.

In the context of the present invention, a "solvent" serves for the dilution of 1-[(4R)-4-methylcyclohexen-1-yl]ethanone to be used according to the invention without having its own odiferous properties. Some solvents have fixing properties at the same time.

The one or more solvent(s) can be present in the composition from 0.01 to 99% by weight based on the composition. In a preferred embodiment of the invention, the composition comprises 0.1 to 90 weight %, preferably 0.5 to 80 weight % of solvent(s) based on the composition. The amount of solvent(s) can be chosen depending on the composition. In one embodiment of the invention, the composition comprises 0.05 to 10 weight %, preferably 0.1 to 5 weight %, more preferably 0.2 to 3 weight % of solvent(s) based on the composition. In one embodiment of the invention, the composition comprises 20 to 70 weight %, preferably 25 to 50 weight % of solvent(s) based on the composition.

Preferred solvents are ethanol, dipropylene glycol (DPG), propylene glycol, 1,2-butylene glycol, glycerol, diethylene glycol monoethyl ether, diethyl phthalate (DEP), isopropyl myristate (IPM), triethyl citrate (TEC), and benzyl benzoate (BB).

Especially preferred solvents are selected from the group consisting of ethanol, propylene glycol, dipropylene glycol, triethyl citrate, benzyl benzoate and isopropyl myristate.

In a preferred embodiment of the invention, the solvent is selected from the group consisting of ethanol, isopropanol, diethylene glycol monoethyl ether, glycerol, propylene glycol, 1,2-butylene glycol, dipropylene glycol, triethyl citrate and isopropyl myristate.

According to a further aspect, 1-[(4R)-4-methylcyclohexen-1-yl]ethanone is suitable for use in surfactant-containing compositions. This is because aroma chemicals with a ylang-ylang note are often sought—especially for the perfuming of surfactant-containing compositions such as, for example, cleaners (in particular dishwashing compositions and all-purpose cleaners).

One embodiment of the invention is therefore directed to a composition comprising 1-[(4R)-4-methylcyclohexen-1-yl]ethanone and at least one surfactant.

In one embodiment of the invention, the compositions according to the invention contain at least one surfactant. The surfactant(s) may be selected from anionic, non-ionic, cationic and/or amphoteric or zwitterionic surfactants. Surfactant-containing compositions, such as for example shower gels, foam baths, shampoos, etc., preferably contain at least one anionic surfactant.

The compositions according to the invention usually contain the surfactant(s), in the aggregate, in a quantity of 0 to 40% by weight, preferably 0 to 20% by weight, more preferably 0.1 to 15% by weight, and still more particularly 0.1 to 10% by weight, based on the total weight of the composition. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Zwitterionic surfactants are surface-active compounds which contain at least one quaternary ammonium group and at least one —COO$^{(-)}$ or —SO$_3$$^{(-)}$ group in the molecule. Particularly suitable zwitterionic surfactants are the so-called betaines, such as the N-alkyl-N,N-dimethyl ammonium glycinates, for example, cocoalkyl dimethyl ammonium glycinate, N-acylaminopropyl-N,N-dimethyl ammonium glycinates, for example, cocoacylaminopropyl dimethyl ammonium glycinate, and 2-alkyl-3-carboxymethyl-3-hydroxyethyl imidazolines, containing 8 to 18 carbon atoms in the alkyl or acyl group, and cocoacylaminoethyl hydroxyethyl carboxymethyl glycinate. The fatty acid amide derivative known under the CTFA name of Cocamidopropyl Betaine is particularly preferred.

Ampholytic surfactants are also suitable, particularly as co-surfactants. Ampholytic surfactants are surface-active compounds which, in addition to a C8 to C18 alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and acyl sarcosine.

Anionic surfactants are characterized by a water-solubilizing anionic group such as, for example, a carboxylate, sulfate, sulfonate or phosphate group and a lipophilic group. Dermatologically safe anionic surfactants are known to the practitioner in large numbers from relevant textbooks and are commercially available. They are, in particular, alkyl sulfates in the form of their alkali metal, ammonium or alkanolammonium salts, alkylether sulfates, alkylether carboxylates, acyl isethionates, acyl sarcosinates, acyl taurines containing linear C12-8 alkyl or acyl groups and sulfosuccinates and acyl glutamates in the form of their alkali metal or ammonium salts.

Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example, cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, such as, for example, the dialkyl ammonium methosulfates and methyl hydroxyalkyl dialkoyloxyalkyl ammonium methosulfates marketed under the name of Stepantexe and the corresponding products of the Dehyquart® series, may be used as cationic surfactants. "Esterquats" are generally understood to be quaternized fatty acid triethanolamine ester salts. They can provide the compositions with particular softness. They are known substances which are prepared by the relevant methods of organic chemistry. Other cationic surfactants suitable for use in accordance with the invention are the quaternized protein hydrolyzates.

One embodiment of the invention is directed to a composition comprising 1-[(4R)-4-methylcyclohexen-1-yl]ethanone and at least one oil component.

The oil components are typically present in a total quantity of 0.1 to 80, more particularly 0.5 to 70, preferably 1 to 60, more particularly 1 to 50% by weight, more particularly 1 to 40% by weight, preferably 5 to 25% by weight and more particularly 5 to 15% by weight based on the composition.

The oil components may be selected, for example, from Guerbet alcohols based on fatty alcohols containing 6 to 18 and preferably 8 to 10 carbon atoms and other additional esters, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of C18-C38 alkyl-hydroxycarboxylic acids with linear or branched C6-C22 fatty alcohols, more especially dioctyl malate, esters of linear and/or branched fatty acids with polyhydric alcohols (for example propylene glycol, dimer dial or trimer triol), triglycerides based on C6-C10 fatty acids, liquid mono-, di- and triglyceride mixtures based on C6-C18 fatty acids, esters of C6-C22 fatty alcohols and/or Guerbet alcohols with aromatic carboxylic acids, more particularly benzoic acid, esters of dicarboxylic acids with polyols containing 2 to 10 carbon atoms and 2 to 6 hydroxyl groups, vegetable oils, branched primary alcohols, substituted cyclohexanes, linear and branched C6_22 fatty alcohol carbonates such as, for example, Dicaprylyl Carbonate (Cetiol@ CC), Guerbet carbonates based on fatty alcohols containing 6 to 18 and preferably 8 to 10 carbon atoms, esters of benzoic acid with linear and/or branched C6 to C22 alcohols (for example Finsolv® TN), linear or branched, symmetrical or nonsymmetrical dialkyl ethers containing 6 to 22 carbon atoms per alkyl group such as, for example, Dicaprylyl Ether (Cetiol® OE), ring opening products of epoxidized fatty acid esters with polyols and hydrocarbons or mixtures thereof.

Compositions

1-[(4R)-4-methylcyclohexen-1-yl]ethanone can be used in a wide range of compositions. The olfactory properties, the substance properties (such as solubility in customary solvents and compatibility with further customary constituents of such compositions), as well as the toxicological acceptability of 1-[(4R)-4-methylcyclohexen-1-yl]ethanone underline its particular suitability for the stated use purposes and compositions.

Compositions which comprise 1-[(4R)-4-methylcyclohexen-1-yl]ethanone or in which 1-[(4R)-4-methylcyclohexen-1-yl]ethanone can be used according to the invention are for example perfume compositions, body care compositions, hygiene articles, household cleaning compositions, textile detergent compositions, foods, food supplements, pharmaceutical compositions and crop protection compositions.

Perfume compositions can be selected from fine fragrances, air fresheners in liquid form, gel-like form or a form applied to a solid carrier, aerosol sprays, scented cleaners and oils;

Examples for fine fragrances are perfume extracts, Eau de Parfums, Eau de Toilettes, Eau de Colognes, Eau de Solide and Extrait Parfum.

Body care compositions can be selected from aftershaves, pre-shave products, splash colognes, solid and liquid soaps, shower gels, shampoos, shaving soaps, saving foams, bath oils, cosmetic emulsions of the oil-in-water type, of the water-in-oil type and of the water-in-oil-in-water type, such as e.g. skin creams and lotions, face creams and lotions, sunscreen creams and lotions, aftersun creams and lotions, hand creams and lotions, foot creams and lotions, hair removal creams and lotions, aftershave creams and lotions, tanning creams and lotions, hair care products such as e.g. hairsprays, hair gels, setting hair lotions, hair conditioners, hair shampoo, permanent and semipermanent hair colorants, hair shaping compositions such as cold waves and hair smoothing compositions, hair tonics, hair creams and hair lotions, deodorants and antiperspirants such as e.g. underarm sprays, roll-ons, deodorant sticks, deodorant creams, products of decorative cosmetics such as e.g. eyeshadows, nail varnishes, make-ups, lipsticks, mascara, toothpaste, dental floss;

Hygiene articles can be selected from candles, lamp oils, joss sticks, insecticides, repellents, propellants, rust removers, perfumed freshening wipes, armpit pads, baby diapers, sanitary towels, toilet paper, cosmetic wipes, pocket tissues, dishwasher deodorizer;

Household cleaning compositions, such as e.g. cleaners for solid surfaces can be selected from perfumed acidic, alkaline and neutral cleaners, such as e.g. floor cleaners, window cleaners, dishwashing detergents, bath and sanitary cleaners, scouring milk, solid and liquid toilet cleaners, powder and foam carpet cleaners, waxes and polishes such as furniture polishes, floor waxes, shoe creams, disinfectants, surface disinfectants and sanitary cleaners, brake cleaners, pipe cleaners, limescale removers, grill and oven cleaners, algae and moss removers, mold removers, facade cleaners;

Textile detergent compositions can be selected from liquid detergents, powder detergents, laundry pretreatments such as bleaches, soaking agents and stain removers, fabric softeners, washing soaps, washing tablets.

Food means a raw, cooked, or processed edible substance, ice, beverage or ingredient used or intended for use in whole or in part for human consumption, or chewing gum, gummies, jellies, and confectionaries.

A food supplement is a product intended for ingestion that contains a dietary ingredient intended to add further nutritional value to the diet. A dietary ingredient may be one, or any combination, of the following substances: a vitamin, a mineral, an herb or other botanical, an amino acid, a dietary substance for use by people to supplement the diet by increasing the total dietary intake, a concentrate, metabolite, constituent, or extract. Food supplements may be found in many forms such as tablets, capsules, softgels, gelcaps, liquids, or powders.

Pharmaceutical compositions comprise compositions, which are intended for use in the diagnosis, cure, mitigation, treatment, or prevention of disease as well as articles (other than food) intended to affect the structure or any function of the body of man or other animals.

Crop protection compositions comprise compositions, which are intended for the managing of plant diseases, weeds and other pests (both vertebrate and invertebrate) that damage agricultural crops and forestry.

The compositions according to the invention can further comprise one or more substances, such as, for example: preservatives, abrasives, antiacne agents, agents to combat skin aging, antibacterial agents, anticellulite agents, antidandruff agents, anti-inflammatory agents, irritation-preventing agents, irritation-alleviating agents, antimicrobial agents, antioxidants, astringents, sweat-inhibiting agents, antiseptics, antistatics, binders, buffers, carrier materials, chelating agents, cell stimulants, cleaning agents, care agents, hair removal agents, surface-active substances, deodorizing agents, antiperspirants, emulsifiers, enzymes, essential oils, fibers, film formers, fixatives, foam formers, foam stabilizers, substances for preventing foaming, foam boosters, fungicides, gelling agents, gel-forming agents, hair care agents, hair shaping agents, hair smoothing agents, moisture-donating agents, moisturizing substances, humectant substances, bleaching agents, strengthening agents, stain removal agents, optical brighteners, impregnating agents, soil repellents, friction-reducing agents, lubricants, moisturizing creams, ointments, opacifiers, plasticizers, covering agents, polish, shine agents, polymers, powders, proteins, refatting agents, exfoliating agents, silicones, skin-calming agents, skin-cleansing agents, skin care agents, skin-healing agents, skin lightening agents, skin-protective agents, skin-softening agents, cooling agents, skin-cooling agents, warming agents, skin-warming agents, stabilizers, UV-absorbent agents, UV filters, fabric softeners, suspending agents, skin-tanning agents, thickeners, vitamins, oils, waxes, fats, phospholipids, saturated fatty acids, mono- or polyunsaturated fatty acids, α-hydroxy acids, polyhydroxy fatty acids, liquefiers, dyes, color-protection agents, pigments, anticorrosives, polyols, surfactants, electrolytes, organic solvents or silicone derivatives.

1-[(4R)-4-methylcyclohexen-1-yl]ethanone used according to the invention and the compositions comprising 1-[(4R)-4-methylcyclohexen-1-yl]ethanone according to the invention can also be in microencapsulated form, spray-dried form, in the form of inclusion complexes or in the form of extrusion products. The properties can be further optimized by so-called "coating" with suitable materials with regard to a more targeted release of the scent, for which purpose preferably waxy synthetic substances such as e.g. polyvinyl alcohol are used.

The microencapsulation can take place for example by the so-called coacervation method with the help of capsule materials, e.g. made of polyurethane-like substances or soft gelatin. The spray-dried perfume oils can be produced for example by spray-drying an emulsion or dispersion comprising the 1-[(4R)-4-methylcyclohexen-1-yl]ethanone, wherein carrier substances that can be used are modified starches, proteins, dextrin and vegetable gums. Inclusion complexes can be prepared e.g. by introducing dispersions of fragrance compositions and cyclodextrins or urea derivatives into a suitable solvent, e.g. water. Extrusion products can be produced by melting 1-[(4R)-4-methylcyclohexen-1-yl]ethanone with a suitable wax-like substance and by extrusion with subsequent solidification, optionally in a suitable solvent, e.g. isopropanol.

The compositions according to the invention can comprise 1-[(4R)-4-methylcyclohexen-1-yl]ethanone from 0.05 to 99.9% by weight, preferably from 0.1 to 90% by weight, preferably from 0.5 to 80% by weight based on the total weight of the composition.

In one embodiment of the invention, the compositions comprise 1-[(4R)-4-methylcyclohexen-1-yl]ethanone from 0.05 to 15 weight %, preferably from 0.1 to 10 weight % based on the total weight of the composition.

In one embodiment of the invention, the compositions comprise 1-[(4R)-4-methylcyclohexen-1-yl]ethanone from 0.1 to 5 weight %, preferably from 0.2 to 2 weight % based on the total weight of the composition.

Method of Preparing a Composition

A further embodiment of the invention is directed to a method of preparing a perfume composition, body care composition, hygiene article, household cleaning composition, textile detergent composition, food, food supplement, pharmaceutical composition or crop protection composition, comprising including 1-[(4R)-4-methylcyclohexen-1-yl] ethanone in a perfume composition, body care composition, hygiene article, household cleaning composition, textile detergent composition, food, food supplement, pharmaceutical composition or crop protection composition.

In one embodiment of the invention, 1-[(4R)-4-methylcyclohexen-1-yl] imparts a ylang-ylang note to these compositions.

In one embodiment of the invention, 1-[(4R)-4-methylcyclohexen-1-yl]ethanone is included as a mixture comprising 1-[(4R)-4-methylcyclohexen-1-yl]ethanone and 1-[(4S)-4-methylcyclo-hexen-1-yl]ethanone, wherein the amount of 1-[(4R)-4-methylcyclohexen-1-yl]ethanone exceeds the amount of 1-[(4S)-4-methylcyclohexen-1-yl]ethanone.

The present invention encompasses the use of 1-[(4R)-4-methylcyclohexen-1-yl]ethanone or compositions comprising 1-[(4R)-4-methylcyclohexen-1-yl]ethanone, wherein 1-[(4R)-4-methylcyclohexen-1-yl]ethanone is used either as 1-[(4R)-4-methylcyclohexen-1-yl]ethanone itself or as a mixture comprising 1-[(4R)-4-methylcyclohexen-1-yl]ethanone and 1-[(4S)-4-methylcyclo-hexen-1-yl]ethanone, wherein the amount of 1-[(4R)-4-methylcyclohexen-1-yl] ethanone exceeds the amount of 1-[(4S)-4-methylcyclohexen-1-yl]ethanone.

1-[(4R)-4-methylcyclohexen-1-yl]ethanone can be manufactured as described in Taber et al. (J. Org. Chem., 44, No 3, 450-452, 1979) page 450. 1-[(4R)-4-methylcyclohexen-1-yl]ethanone can also be manufactured by ozonolysis of L-Isopulegol as described in the yet unpublished PCT application PCT/US2016/051334.

EXAMPLES

1-[(4R)-4-methylcyclohexen-1-yl]ethanone was prepared as follows:

Example 1a: Synthesis of Compound (VI) from Compound (III)

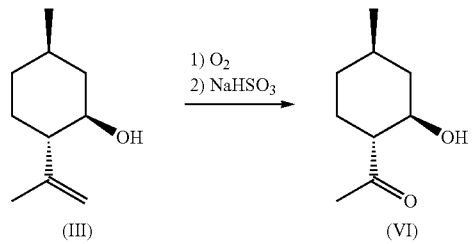

L-Isopulegol (=Compound III) (150 g, 0.97 mmol) was combined with $H_2O$ (300 mL) and the mixture was cooled to 10° C. in a jacketed glass reactor equipped with an overhead stirrer and gas diffuser. An $O_3/O_2$ mixture was bubbled through the reaction for 5 hours making sure the reaction did not exceed 15° C. Following complete consumption of starting material, 121 g of $NaHSO_3$ was added at 0° C. and was allowed to warm to room temperature overnight. The aqueous phase was then extracted with MTBE (350 mL×2), washed with $Na_2CO_3$ (10% aqueous), and then dried with $Na_2SO_4$, filtered, and concentrated.

This resulted in 138.7 g of white crystalline solid, 91.3% of theoretical yield, with an estimated purity of 97.9%. $^1$H NMR (CDCl$_3$, 500 MHz), δ 0.87 (d, J=6.5 Hz, 3H, —CH$_3$), 0.86-0.96 (m, 2H, —CH$_2$—), 1.16-1.25 (m, 1H, —CH$_2$—), 1.37-1.44 (m, 1H, —CH$_3$), 1.62-1.67 (m, 1H, —CH$_2$—), 1.84-1.91 (m, 2H, —CH$_2$—), 2.10 (s, 3H, —CH$_3$), 2.22-2.27 (m, 1H, —CH—), 3.00 (s, broad, 1H, —OH), 3.71-3.76 (m, 1H, —CHO—).

Example 1 b: Synthesis of Compound (I) from Compound (VI)

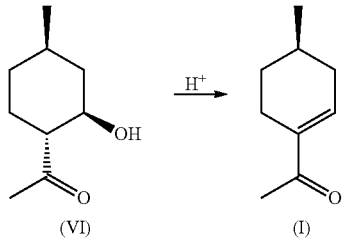

230 g (1.47 mol) of compound (VI) was dissolved in 500 ml of Toluene, charged with 4.6 g of Amberlyst® 15 catalyst, and was placed in a round bottomed flask equipped with a Dean Stark apparatus for removal of water. The mixture was heated at 80-140° C., including all ranges and subranges there between, and more preferably, at 110-130° C. for 7 hours until all water had appeared to stop forming. In some embodiments, dehydration was performed continuously. The Amberlyst® was then filtered out and the toluene was removed. The isolated residue was then distilled at around 1.0 mbar and 65-70° C. (42-48° C. head temperature) to obtain 173.2 g of >97% pure desired product, (R)-1-(4- methylcyclohex-1-en-1-yl)ethanone (i.e., compound (I)): $^1$H NMR (CDCl$_3$, 500 MHz), δ 0.97 (d, J=6.5 Hz, 3H, —CH$_3$), 1.13-1.21 (m, 1H, —CH$_2$—), 1.61-1.67 (m, 1H, —CH$_2$—), 1.80-1.88 (m, 1H, —CH$_2$—), 2.05-2.14 (m, 1H, —CH$_2$—), 2.27 (s, 3H, —CH$_3$), 2.30-2.45 (m, 2H, —CH$_2$—), 6.85 (m, 1H, —CH=C).

Olfactory Assessment:

A 1% weight solution of 1-[(4R)-4-methylcyclohexen-1-yl]ethanone as obtained in Example 1 in triethylcitrate was prepared and evaluated by a panel of 4 professional perfumers at room temperature at about 20° C. using freshly dipped blotter paper. The olfactory notes were ranked from 1 (very weak) to 6 (strong).

| Olfactory note | Ylang-Ylang | Dark Cherry | Almond | Camphoraceous |
|---|---|---|---|---|
| Example 1 | 5 | 4 | 4 | 4 |

Example 2: The Following Perfume Compositions were Prepared

| COLOGNE SPORT TYPE YLANG EFFECT | | | |
|---|---|---|---|
| Formula | A | B | C |
| Spearmint Oil | 2 | 2 | 2 |
| Geranium Oil | 2 | 2 | 2 |
| (2-methyl-1-phenylpropan-2-yl) acetate (D.M.B.C. Acetate) | 5 | 5 | 5 |
| 3a,6,6,9a-tetramethyldodecahydronaphtho[2,1-b]furan (Ambroxan) 10% DPG | 7 | 7 | 6 |
| 3-Methyl-5-(2,2,3-trimethylcyclopent-3-en-1-yl)pentan-2-ol (Sandalore) | 8 | 8 | 7 |
| 2,4-dimethyl-3-cyclohexenecarbaldehyde (Triplal) | 8 | 8 | 8 |
| Coumarin | 9 | 9 | 9 |
| Methyl cedryl ether (Cedramber) | 9 | 9 | 9 |
| 1-phenylethyl acetat (=Styrallyl Acetate) | 9 | 9 | 9 |
| CITRAL | 9 | 9 | 9 |
| Geraniol Extra | 9 | 9 | 9 |
| Anisaldehyde | 9 | 9 | 9 |
| Dihydrorose oxide (Dihydrorosan) | 9 | 9 | 9 |
| Rosemary Oil | 11 | 11 | 11 |
| Petit Grain Oil | 14 | 14 | 14 |
| Gamma-Methylionone | 19 | 19 | 18 |
| 1-(5,6,7,8-tetrahydro-3,5,5,6,8,8-hexamethyl-2-naphthalenyl)ethanone (Tonalide) | 19 | 19 | 18 |
| 2-isobutyl-4-methyltetrahydro-2H-pyran-4-ol | 28 | 28 | 90 |
| p-Cresylmethylether | 28 | 0 | 0 |
| 1-[(4R)-4-methylcyclohexen-1-yl]ethanone | 0 | 28 | 81 |
| Sweet Orange Oil | 38 | 38 | 36 |
| 2-acetyl-1,2,3,4,6,7,8-octahydro-2,3,8,8-tetramethylnaphthalene (Iso E Super) | 38 | 38 | 36 |
| (6E)-3,7-dimethylnona-1,6-dien-3-ol (Ethyl Linalool) | 57 | 57 | 54 |
| Lemon Oil Italy | 75 | 75 | 72 |
| Ethyl Linalyl Acetate | 75 | 75 | 72 |
| 2,6-dimethyloct-7-en-2-ol (Dihydromyrcenol) | 85 | 85 | 81 |
| Methyl 2-(3-oxo-2-pentylcyclopentyl)acetate (Hedione) | 104 | 104 | 99 |
| Bergamote Base | 311 | 311 | 225 |
| ad | 1000 | 1000 | 1000 |

Trade names or trivial names are given in brackets.

In Formula A (comparative composition) a cologne Sport formulation is characterized in it's fresh but valuable impression by the content of p-Cresylmethylether.

In Formula B (composition according to the invention) p-Cresylmethylether is replaced by 1-[(4R)-4-methylcyclohexen-1-yl]ethanone. The odiferous character as compared to Formula A is not only maintained but the almond-camphoraceous note appears more delicious and contributes to an overall improved odor.

In Formula C (composition according to the invention) the amount of 1-[(4R)-4-methylcyclohexen-1-yl]ethanone has been increased together with the amount of 2-isobutyl-4-methyltetrahydro-2H-pyran-4-ol, resulting in a nice effect of valuable Daffodil and Ylang-Ylang facets.

The invention claimed is:

1. An aroma chemical comprising 1-[(4R)-4-methylcyclohexen-1-yl]ethanone.

2. A mixture comprising 1-[(4R)-4-methylcyclohexen-1-yl]ethanone and 1-[(4S)-4-methylcyclo-hexen-1-yl]ethanone, wherein the amount of 1-[(4R)-4-methylcyclohexen-1-yl]ethanone exceeds the amount of 1-[(4S)-4-methylcyclohexen-1-yl]ethanone.

3. A composition comprising 1-[(4R)-4-methylcyclohexen-1-yl]ethanone and at least one further aroma chemical.

4. A composition comprising 1-[(4R)-4-methylcyclohexen-1-yl]ethanone and at least one compound selected from the group consisting of surfactants, oil components and solvents, wherein the solvent is not diethylether.

5. The composition according to claim 3, selected from perfume compositions, body care compositions, hygiene articles, household cleaning compositions, textile detergent compositions, foods, food supplements, pharmaceutical composition and crop protection composition.

6. The composition according to claim 3, comprising 1-[(4R)-4-methylcyclohexen-1-yl]ethanone from 0.1 to 99.9% by weight, based on the total weight of the composition.

7. A method of preparing a perfume composition, body care composition, hygiene article, household cleaning composition, textile detergent composition, food, food supplement, pharmaceutical composition or crop protection composition, comprising including 1-[(4R)-4-methylcyclohexen-1-yl]ethanone in a perfume composition, body care composition, hygiene article, household cleaning composition, textile detergent composition, food, food supplement, pharmaceutical composition or crop protection composition.

8. The method of claim 7, wherein 1-[(4R)-4-methylcyclo hexen-1-yl] imparts a ylang-ylang note to the perfume composition, body care composition, hygiene article, household cleaning composition, textile detergent composition, food, food supplement, pharmaceutical composition or crop protection composition.

9. The method of claim 7, wherein 1-[(4R)-4-methylcyclohexen-1-yl]ethanone is included as a mixture according to claim 2.

* * * * *